US008664428B2

(12) United States Patent
Fischer et al.

(10) Patent No.: US 8,664,428 B2
(45) Date of Patent: Mar. 4, 2014

(54) METHOD FOR PRODUCING (2,4-DIMETHYLBIPHENYL-3-YL)ACETIC ACIDS, THE ESTERS THEREOF AND INTERMEDIATE COMPOUNDS

(75) Inventors: Reiner Fischer, Monheim (DE); Thomas Himmler, Odenthal (DE); Wolfgang Joerges, Odenthal (DE); Werner Lindner, Cologne (DE); Wahed Ahmed Moradi, Monheim (DE)

(73) Assignee: Bayer CropScience AG, Monheim (DE)

( * ) Notice: Subject to any disclaimer, the term of this patent is extended or adjusted under 35 U.S.C. 154(b) by 125 days.

(21) Appl. No.: 13/382,847

(22) PCT Filed: Jun. 25, 2010

(86) PCT No.: PCT/EP2010/003911
§ 371 (c)(1),
(2), (4) Date: Jan. 6, 2012

(87) PCT Pub. No.: WO2011/003530
PCT Pub. Date: Jan. 13, 2011

(65) Prior Publication Data
US 2012/0116118 A1    May 10, 2012

(30) Foreign Application Priority Data
Jul. 7, 2009    (EP) .................................... 09164792

(51) Int. Cl.
*C07C 67/343* (2006.01)
*C07C 67/317* (2006.01)
*C07C 67/327* (2006.01)
*C07C 67/307* (2006.01)
*C07C 69/612* (2006.01)

(52) U.S. Cl.
USPC ........................................... 560/102; 560/60

(58) Field of Classification Search
None
See application file for complete search history.

(56) References Cited

U.S. PATENT DOCUMENTS

| 2,860,169 A | 11/1958 | Schlatter et al. |
| 5,306,833 A | 4/1994 | Vallejos et al. |
| 5,994,274 A | 11/1999 | Fischer et al. |
| 6,140,358 A | 10/2000 | Lieb et al. |
| 2003/0181748 A1 | 9/2003 | Krauter et al. |
| 2006/0160847 A1 | 7/2006 | Fischer et al. |
| 2008/0188371 A1 | 8/2008 | Fischer et al. |
| 2011/0306499 A1 | 12/2011 | Bretschneider et al. |

FOREIGN PATENT DOCUMENTS

| WO | WO 97/36868 A1 | 10/1997 |
| WO | WO 2005/016873 A2 | 2/2005 |
| WO | WO 2008/067911 A1 | 6/2008 |

OTHER PUBLICATIONS

"Bis(Chloromethyl) Ether in Chloromethylations—Warning" in *Organic Reactions*, vol. 19, p. 422,—Dabuen, W.G., Ed., Wiley-VCH, Germany (1972).
"Preparation, Applications in Organic Synthesis and Medicine," in *Boronic Acids*, p. 28-36, Hall, D.G., Ed., Wiley-VCH, Germany (2005).
Anulewicz-Ostrowska, R., et al., "Synthesis of some halogenated tetraarylborates," *Tetrahedron Letters* 44:7329-7331, Elsevier Ltd., England (2003).
Bellina, F., et al., "Palladium Catalysts for the Suzuki Cross-Coupling Reaction: An Overview of Recent Advances," *Synthesis* 15:2419-2440, Thieme, Stuttgart, Germany (2004).
Brown, H.C., and Gupta, A.K., "XVI. Boroxazolidones derived from α-amino acids and borinic or boronic esters. A simple procedure for upgrading borinates and boronates to materials of high optical purity," *Journal of Organometallic Chemistry* 341:73-81, Elsevier Sequoia S.A., Switzerland (1988).
Buu-Hoi and Cagniant, P., "Cleavage and Migration of Tert-Butyl Radicals During Chemical Reactions. II. 1,3-Dimethyl-5-tert-butylbenzene and Its Derivatives et des ses derivés," *Bull. Soc. Chim. de Fr.* 9:889-892, France (1942).
Crawford, M., and Magill, J.H., "The Preparation of Some Alkyl-substituted Benzoic Acids," *J. Chem. Soc.*:3275-3278, British Chemical Society, England (1957).
Dai, C., and Fu, G.C., "The First General Method for Palladium-Catalyzed Negishi Cross-Coupling of Aryl and Vinyl Chlorides: Use of Commercially Available Pd(P(t-Bu)$_3$)$_2$ as a Catalyst," *J. Am. Chem. Soc.* 123:2719-2724, American Chemical Society, United States (2001).
Darses, S., and Genet, J-P., "Potassium Organotrifluoroborates: New Perspectives in Organic Synthesis," *Chem. Rev.* 108:288-325, American Chemical Society, United States (2008).
Dozeman, G.J., et al., "Chemical Development of a Pilot Scale Process for the ACAT Inhibitor 2,6-Diisopropylphenyl [(2,4,6-Triisopropylphenyl)acetyl]sulfamate," *Organic Process Research & Development* 1(2):137-148, American Chemical Society and Royal Society of Chemistry, United States (1997).
Heitmann, W., et al., "Ethers, Aliphatic," in *Ullmann's Encyclopedia of Industrial Chemistry*, vol. A 10, p. 23, 31-34, Wiley-VCH, Germany (2009).
Ito, T., et al., "Palladium-Catalyzed Cross-Coupling Reaction of Potassium Diaryldifluoroborates with Aryl Halides," *Synlett* 10:1435-1438, Thieme, Stuttgart, Germany (2003).
Löfgren, N., et al., "Syntheses of three Xylocaine® Analogues. Steric Effects in the Reaction between 2,6-Dimethylphenyllithium and Epichlorohydrin," *Acta Chem. Scand* 17(5):1252-1261, Society for the Publication of Acta Chirurgica Scandinavica, Sweden (1963).
Miescher, K., and Billeter, J.R., "Über Reduktionen mit Phosphor in Gegenwart von Jod bzw. Jodwasserstoff als Katalysator," *Helv. Chim. Acta* 22:601-610, Schweizerische Chemische Gesellschaft, Switzerland (1939).

(Continued)

*Primary Examiner* — Brian J Davis
(74) *Attorney, Agent, or Firm* — Sterne, Kessler, Goldstein & Fox P.L.L.C.

(57) ABSTRACT

The present invention relates to a novel process for preparing substituted and unsubstituted (2,4-dimethylbiphenyl-3-yl) acetic acids and their esters of the formula (I) using homogeneous and heterogeneous palladium catalysts, and also the intermediates 4-tert-butyl-2,6-dimethylphenylacetic acid and 4-tert-butyl-2,6-dimethylmandelic acid, and to processes for their preparation.

9 Claims, No Drawings

(56) References Cited

OTHER PUBLICATIONS

Miyaura, N., and Suzuki, A., "Palladium-Catalyzed Cross-Coupling Reactions of Organoboron Compounds," *Chem. Rev.* 95:2457-2483, American Chemical Society, United States(1995).

Otsuka, S., et al., "Bis( tertiary phosphine)palladium(0) and -platinum(0) Complexes: Preparations and Crystal and Molecular Structures," *J. Am. Chem. Soc.* 98(19):5850-5858, American Chemical Society, United States (1976).

Pelter, A., et al., "Transmetallation Reactions for Preparation of Organoboron Compounds," in *Borune Reagents*, pp. 227-228, Harcourt Brace Jovanovich, United States (1988).

Washburn, R.M., et al., "Benzeneboronic Anhydride," in *Organic Syntheses Collective*, vol. 4, pp. 68-72, John Wiley & Sons, United States (1963).

Van Zanten, B., and Nauta, W.T., "Synthesis of Alkyl-Substituied 3-Phenyl-4-Hydroxycoumarins" *RECUEIL* 79:1211-1222, Wiley-VCH, Germany (1960).

Yoshida, T., and Otsuka, S. "Reactions of Two-Coordinate Phosphine Platinum(0) and Palladium(0) Compounds. Ligand Exchange and Reactivities toward Small Molecules," *J. Am. Chem. Soc.* 99(7):2124-2140, American Chemical Society, United States (1977).

International Search Report for International Application No. PCT/EP2010/003911, European Patent Office, The Hague, Netherlands, mailed on Dec. 22, 2010.

METHOD FOR PRODUCING (2,4-DIMETHYLBIPHENYL-3-YL)ACETIC ACIDS, THE ESTERS THEREOF AND INTERMEDIATE COMPOUNDS

The present invention relates to a process for preparing substituted and unsubstituted (2,4-dimethylbiphenyl-3-yl) acetic acids and their esters using homogeneous and heterogeneous palladium catalysts, and also the intermediates 4-tert-butyl-2,6-dimethylphenylacetic acid and 4-tert-butyl-2,6-dimethylmandelic acid, and to processes for their preparation.

Biaryl compounds, in particular biphenyl compounds, are important intermediates, for example in the preparation of pharmaceutical compounds or agrochemicals (see, for example, EP-A-835243; WO2004/065366).

A method frequently used for synthesizing biaryls is the Suzuki reaction in which iodo- or bromoaromatics and in exceptional cases chloroaromatics are reacted with arylboronic acid derivatives in the presence of homogeneous and heterogeneous palladium catalysts. Reviews describing this method can be found, for example, in N. Miyaura, A. Suzuki, Chem. Rev. 1995, 95, 2457 and Bellina, F. et al., Synthesis 2004, 2419. EP-A-1 186 583 teaches the use of supported Pd catalysts.

All homogeneous processes use palladium complexes which are expensive or difficult to prepare, or it is required to work in the presence of an excess of arylboronic acid to achieve a good yield. This not only increases the costs of the process by loss of valuable arylboronic acid, but also by more complicated purification and isolation processes required to remove excess boronic acid and the byproducts formed therefrom, such as deboronated aromatics and homocoupling products.

The course of the Suzuki reaction is also influenced decisively by the reactivity of the boronic acid or borinic acid used, where in particular aromatics deactivated by electron-withdrawing substituents react more slowly and may give homocoupling products. However, this problem is rarely addressed in the methodically orientated literature as in most cases the reactions are carried out in a large excess of boronic acid and the yields are based only on the conversion of the halogenated aromatic. A further disadvantage of the processes described in the prior art is thus the competing homocoupling reaction of the halogenated aromatics with formation of "symmetrical" biphenyls.

With a view to the disadvantages and problems described above, there is an urgent need for a simplified process which can be carried out on an industrial scale and in an economic manner for the selective Suzuki coupling of substituted and unsubstituted phenylacetic acids on an industrial scale and using easily accessible and cheap starting materials.

It is an object of the present invention to provide a novel process for preparing biaryls which does not have the disadvantages of the known processes, is suitable for realization on an industrial scale and affords biaryl compounds in high yield and purity at optimal catalyst productivity.

It has now been found that substituted and unsubstituted (2,4-dimethylbiphenyl-3-yl)acetic acids and their esters of the formula (I) are obtained in a surprising high yield and isomeric purity by initially reacting 1-tert-butyl-3,5-dimethylbenzene with glyoxylic acid or glyoxylic esters of the formula (VI) to give 4-tert-butyl-2,6-dimethylmandelic acid and their esters of the formula (V) and then reducing these by methods known in principle to 4-tert-butyl-2,6-dimethylphenylacetic acid and their esters of the formula (IV); these for their part are converted by removal of the tert-butyl radical into compounds of the formula (III), and bromination gives compounds of the formula (II) which are converted into biphenyl compounds of the formula (I) using homogeneous and heterogeneous palladium catalysts.

The process according to the invention can be illustrated by the scheme below:

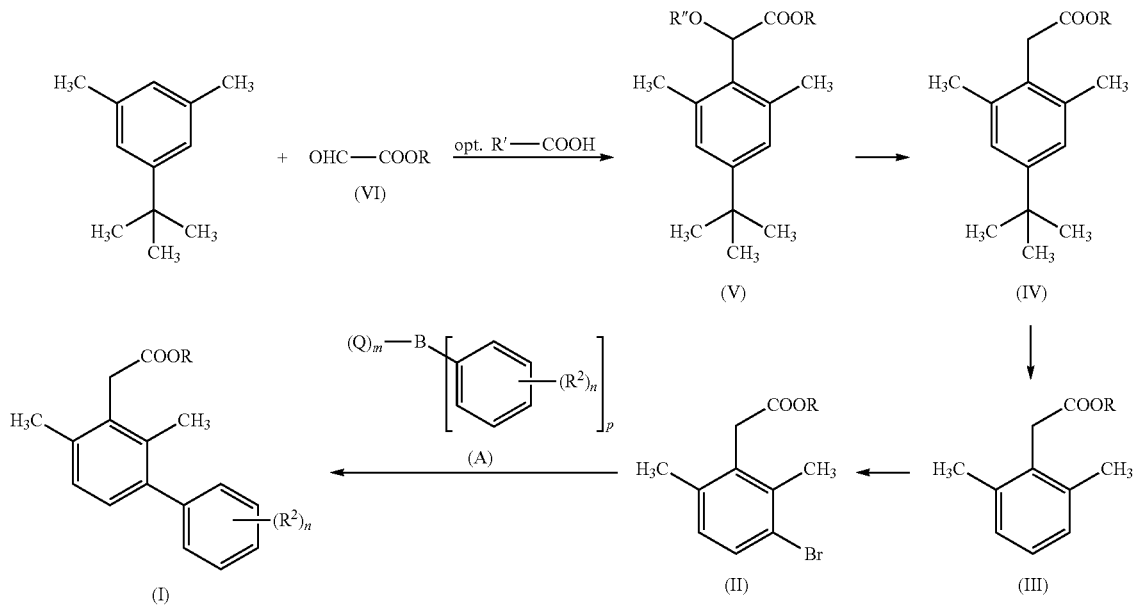

Halogenated phenylacetic acids and their esters are important precursors for preparing, for example, biphenyl compounds.

Feasible methods for synthesizing 4-tert-butyl-2,6-dimethylphenylacetic acid may start, for example, with 5-tert-butyl-meta-xylene (1-tert-butyl-3,5-dimethylbenzene). It is already known to subject 1-tert-butyl-3,5-dimethylbenzene to a chloromethylation (Buu-Hoi and P. Cagniant, *Bull. soc. chim.* 1942, 889-92; M. Crawford and J. H. Magill, *J. Chem, Soc.* 1957, 3275-8; M. J. Schlatter, U.S. Pat. No. 2,860,169

(*California Research Comp.*, 1958)). After cyanation with an alkali metal cyanide, the nitrile obtained in this manner can be hydrolyzed to give the corresponding phenylacetic acid (Buu-Hoi and P. Cagniant, *Bull. soc. chim.* 1942, 889-92).

This method has the serious disadvantage that it is known (*Organic Reactions* 19 (1972) 422; *Ullmann's Encyclopedia of Industrial Chemistry*, 2009, *Topic "Ethers"*) that under the conditions of the chloromethylation the highly toxic bis(chloromethyl) ether is formed, too. As a consequence, technically complicated and expensive precautionary measures have to be taken to avoid possible contact with the bis(chloromethyl) ether.

Instead of a chloromethylation, it is also possible to carry out a bromomethylation as the first step of this synthesis method. However, contact with bis(bromomethyl ether) has to be avoided, too.

Another alternative of preparing certain substituted phenylacetic acids consists in the acylation of the corresponding substituted aromatics in a Friedel-Crafts reaction with dichloroacetyl chloride, converting the resulting 2,2-dichloro-1-arylethanone with an alkali metal hydroxide into the substituted mandelic acid and then ultimately reducing this to the phenylacetic acid.

However, it has been found that, in Friedel-Crafts reactions of 1-tert-butyl-3,5-dimethylbenzene with dichloroacetyl chloride, mixtures of mass-isomeric products are formed. These isomeric products may be formed either by an unselective reaction of the 1-tert-butyl-3,5-dimethylbenzene with dichloroacetyl chloride or by an isomerization either of the 1-tert-butyl-3,5-dimethylbenzene or of Friedel-Crafts products in the presence of the Friedel-Crafts catalyst.

Accordingly, this synthesis route is not suitable for preparing 4-tert-butyl-2,6-dimethylmandelic acid and therefrom 4-tert-butyl-2,6-dimethylphenylacetic acid in a simple manner with good yield and purity.

As substituted phenylacetic acids and their esters including 4-tert-butyl-2,6-dimethylphenylacetic acid and its esters are important precursors for biphenyl compounds which for their part are of importance as precursors for active compounds in crop protection, there is a need for a technically simple method for preparing 4-tert-butyl-2,6-dimethylphenylacetic acid and its esters.

It has now been found that 4-tert-butyl-2,6-dimethylphenylacetic acid and its esters of the formula (IV) are obtained in a surprisingly high yield and isomeric purity by initially reacting 1-tert-butyl-3,5-dimethylbenzene with glyoxylic acid or glyoxylic esters of the formula (VI) to give 4-tert-butyl-2,6-dimethylmandelic acid and its esters of the formula (V) and then reducing these by methods known in principle to give 4-tert-butyl-2,6-dimethylphenylacetic acid and its esters of the formula (IV).

Based on the results of the Friedel-Crafts reactions, it was not to be expected that the condensation of the 1-tert-butyl-3,5-dimethylbenzene with glyoxylic acid would take place with such a high selectivity and yield.

The process according to the invention can be illustrated by the scheme below:

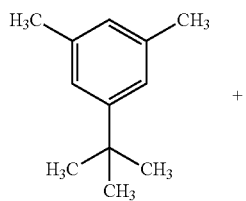

+

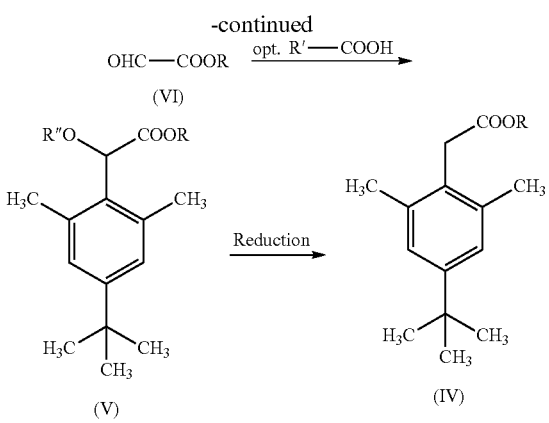

In the formulae (VI), (V) and (IV),
R represents hydrogen, $C_1$-$C_6$-alkyl or phenyl,
R' represents hydrogen or $C_1$-$C_6$-alkyl,
R" represents hydrogen or a radical R'CO.
Preferably,
R represents hydrogen or $C_1$-$C_6$-alkyl,
R' represents $C_1$-$C_6$-alkyl,
R" represents hydrogen or a radical R'CO.
Particularly preferably,
R represents hydrogen or methyl (especially hydrogen),
R' represents $C_1$-$C_6$-alkyl (especially methyl),
R" represents hydrogen or a radical R'CO.

4-tert-Butyl-2,6-dimethylmandelic acid and its esters have hitherto not been disclosed. Accordingly, the compounds of the formula (V) are novel and form part of the subject matter of the present invention. The compounds of the formula (IV) are known from the literature.

In the definitions of the symbols given in the formulae above, collective terms were used which are generally representative for the following substituents:

Halogen: fluorine, chlorine, bromine or iodine.

Alkyl: saturated straight-chain or branched hydrocarbon radicals having 1 to 6 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Suitable solvents for the first step of the process according to the invention are inert organic solvents such as, for example, methylene chloride, toluene, chlorobenzene, formic acid, acetic acid, propionic acid, or water.

Suitable compounds of the formula (VI) are glyoxylic acid, methyl glyoxylate, ethyl glyoxylate, propyl glyoxylate, butyl glyoxylate and phenyl glyoxylate.

Preference is given to using glyoxylic acid, methyl glyoxylate or ethyl glyoxylate.

Very particular preference is given to glyoxylic acid.

When glyoxylic acid is used, the reaction is preferably carried out in a solvent mixture of water and an organic acid such as, for example, formic acid, acetic acid or propionic acid. The glyoxylic acid can be employed, for example, as a commercial 50% strength aqueous solution or as glyoxylic acid hydrate.

Preference is given to a mixture of water and acetic acid or propionic acid.

Particular preference is given to a mixture of water and acetic acid.

The amount of glyoxylic acid or glyoxylic acid hydrate to be used is based on 1-tert-butyl-3,5-dimethylbenzene and is from 0.9 to 2 mol of glyoxylic acid or glyoxylic acid hydrate per mole of 1-tert-butyl-3,5-dimethylbenzene. Preference is given to from 1 to 1.5 mol of glyoxylic acid or glyoxylic acid hydrate per mole of 1-tert-butyl-3,5-dimethylbenzene.

Suitable catalysts are strong organic acids and inorganic acids, such as, for example, para-toluenesulfonic acid, trifluoromethanesulfonic acid, phosphoric acid, hydrochloric acid or sulfuric acid.

Preference is given to using sulfuric acid.

The acids can be employed in amounts of from 0.1 to 200 mol percent based on the amount of glyoxylic acid or glyoxylic acid hydrate used. Preference is given to amounts of from 1 to 1.80 mol percent; particular preference is given to amounts of from 5 to 150 mol percent.

The first step of the process according to the invention can be carried out at temperatures between 0 and 100° C. Preference is given to temperatures between 20 and 80° C.

The reaction times for the first step of the process according to the invention are between 1 and 24 hours.

The reaction is usually carried out under atmospheric pressure; however, in principle it can also be carried out under elevated or reduced pressure.

If the first step of the process according to the invention is carried out in the presence of an organic acid such as, for example, acetic acid or propionic acid, mixtures of mandelic acid and mandelic acid carboxylate, for example mandelic acid acetate or mandelic acid propionate, are naturally obtained.

Such a mixture can then be simplified by alkaline or acidic hydrolysis to afford the mandelic acid, and this product can then be used for the second step of the process according to the invention. However, it is also possible to use the fixture of mandelic acid and mandelic acid carboxylate in the second step of the process according to the invention.

The second step of the process according to the invention can be carried out by methods known in principle. Thus, it is possible, for example, to reduce mandelic acids on a catalyst with hydrogen to give the corresponding phenylacetic acid (see, for example, EP-A-554 636).

An alternative is the reduction of mandelic acid with iodide. The iodide can be employed, for example, in the form of hydroiodic acid (*Org. Process Res. & Dev.* 1 (1997) 137-48). In addition, it is also possible to operate with substoichiometric amounts of iodide in the presence of a strong acid and to re-reduce in situ the iodine formed, using, for example, red phosphorus (see, for example, *Helv. Chim. Acta* 22 (1939) 601-10).

The red phosphorus is employed in the second step of the process according to the invention in amounts of from 0.67 to 3 mol per mole of 4-tert-butyl-2,6-dimethylmandelic acid. Preference is given to from 1 to 2 mol per mole of 4-tert-butyl-2,6-dimethylmandelic acid. Excess red phosphorus can be recovered and re-used.

The iodide source used in the second step of the process according to the invention is hydrogen iodide, KI or NaI. In principle, it is also possible to use iodine. Preference is given to using NaI or KI.

The amount of iodide is from 1 to 30 mol percent (based on 4-tert-butyl-2,6-dimethylmandelic acid); preference is given to using from 5 to 20 mol percent.

Suitable solvents for the second step of the process according to the invention are formic acid, acetic acid, propionic acid, etc., mixtures of these solvents, or 70 to 85% strength aqueous phosphoric acid. Preference is given to from 70 to 85% strength aqueous phosphoric acid and acetic acid; particular preference is given to acetic acid.

The strong acid used in the second step of the process according to the invention is conc. sulfuric acid, conc. hydrochloric acid or 80 to 85% strength aqueous phosphoric acid. Preference is given to conc. sulfuric acid and conc. hydrochloric acid. Particular preference is given to conc. hydrochloric acid.

If the solvent used is 80 to 85% strength aqueous phosphoric acid, the addition of a further acid may naturally be dispensed with.

The second step of the process according to the invention can be carried out at temperatures between +20 and +120° C. Preference is given to temperatures between +60 and +110° C.

The reaction is usually carried out under atmospheric pressure; however, in principle it can also be carried out at elevated or reduced pressure. The reaction times for the second step of the process according to the invention are between 1 and 24 hours.

if the second step of the process according to the invention is carried out using iodide, the isolation of the product of the first step may also be dispensed with, and both steps may be combined in a one-top reaction.

The preparation of 4-tert-butyl-2,6-dimethylphenylacetic acid and its esters by the process according to the invention is to be illustrated by the preparation examples.

Moreover, the present invention relates to a process for preparing 2,6-dimethylphenylacetic acid and its esters of the formula (III), characterized in that 4-tert-butyl-2,6-dimethylphenylacetic acid and its esters of the formula (IV) are reacted in a manner known in principle under conditions under which the tert-butyl radical is removed:

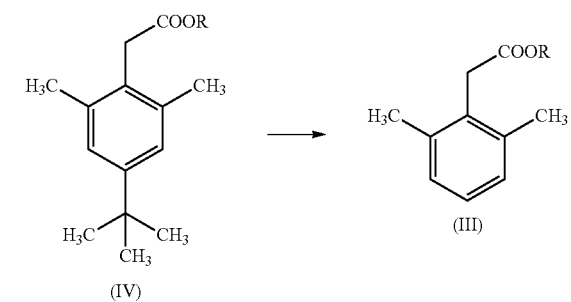

in which R has the meanings given above.

In general, this will take place by transferring the tert-butyl radical of the 4-tert-butyl-2,6-dimethylphenylacetic acid and its esters in the presence of a catalyst to an acceptor.

The acceptor used may be an aromatic hydrocarbon such as, for example, toluene, ortho-xylene, meta-xylene, para-xylene, ethylbenzene or 1,2,4-trimethylbenzene. Preference is given to toluene, ortho-xylene, meta-xylene and para-xylene. Particular preference is given to toluene and meta-xylene.

The acceptor is usually employed in the excess, based on 4-tert-butyl-2,6-dimethylphenylacetic acid or its ester. Here, the amount of acceptor is from 3 to 50 mol per mole of 4-tert-butyl-2,6-dimethylphenylacetic acid or its ester. Preference is given to from 3 to 25 mol per mole.

Suitable catalysts for transferring the tert-butyl radical from the 4-tert-butyl-2,6-dimethylphenylacetic acid or its ester to the acceptor are, in principle, typical Friedel-Crafts catalysts such as $AlCl_3$, $AlBr_3$, $FeCl_3$, HF or strong acidic ion exchangers. The reaction is preferably carried out in anhydrous HF.

The anhydrous HF is usually employed in excess, based on 4-tert-butyl-2,6-dimethylphenylacetic acid or its ester. Here, the amount of anhydrous HF is from 5 to 50 mol per mole of 4-tert-butyl-2,6-dimethylphenylacetic acid or its ester; preference is given to from 7 to 25 mol per mole.

The transfer of the tert-butyl radical from the 4-tert-butyl-2,6-dimethylphenylacetic acid or its ester to the acceptor can be carried out at temperatures between −20 and 150° C. Preference is given to temperatures between 0 and 120° C., particularly preferably between 30 and 80° C.

The reaction is carried out at pressures from 1 to 100 bar, preferably at pressures of from 3 to 20 bar, The reaction times are between 1 and 24 hours.

Moreover, the present invention relates to a process for preparing 3-bromo-2,6-dimethylphenylacetic acid and its esters of the formula (II) by bromination of 2,6-dimethylphenylacetic acid and its esters of the formula (III):

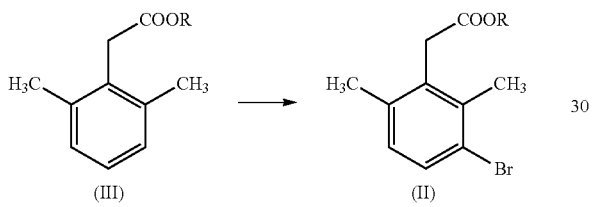

in which R has the meanings given above.

Preferably, the bromination is carried out on 2,6-dimethylphenylacetic acid or its esters of the formula (III) where R=methyl or hydrogen, particularly preferably where R=hydrogen.

Suitable for use as solvents for the bromination are customarily employed inert organic solvents such as, for example, methylene chloride, chloroform, 1,2-dichloroethane, acetic acid or propionic acid. Preference is given to methylene chloride, acetic acid and propionic acid; particular preference is given to acetic acid.

The bromine is usually employed in amounts of from 1 to 2 mol per mole of 2,6-dimethylphenylacetic acid or its esters of the formula (III). Preference is given to amounts of from 1.1 to 1.5 mol per mole.

The reaction temperature for the bromination is between 0 and 100° C. Preference is given to a temperature between 20 and 80° C.

The reaction is usually carried out under atmospheric pressure; however, in principle, it can also be carried out at elevated or reduced pressure.

The reaction time for the bromination is between 1 and 24 hours.

It may be considered very surprising that, in particular even taking into account the results of the analogous chlorination, that this bromination affords the 3-bromo-2,6-dimethylphenylacetic acid or its esters in such a high selectivity and yield (see preparation examples).

Moreover, the present invention relates to a process for preparing biphenyl compounds of the formula (I)

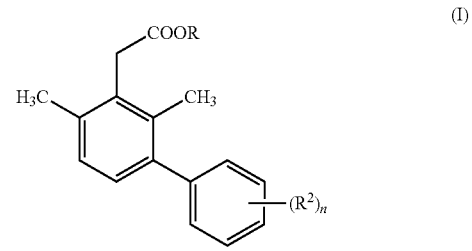

in which

R has the meanings given above, $R^2$ represents hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, cyano, nitro, (preferably hydrogen, halogen or $C_1$-$C_4$-alkyl; particularly preferably hydrogen or fluorine, especially 4-fluoro)

and n represents 0, 1, 2 or 3 (especially 1), characterized in that a compound of the formula (II)

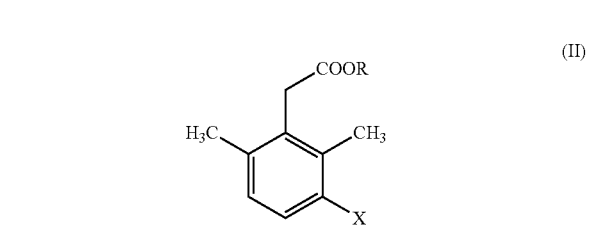

in which

R has the meanings given above and

X represents halogen (preferably chlorine or bromine; particularly preferably bromine) is reacted in the presence of a base and a palladium catalyst, if appropriate in a solvent, with a compound of the formula (A)

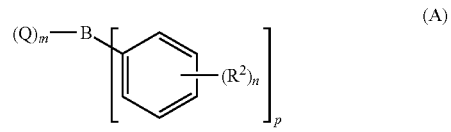

which may be selected from the following groups:

(a) boronic acid of the formula (A-a) in which m represents 2, p represents 1,

Q represents a hydroxyl group, or the anhydrides, dimers and trimers formed therefrom, and $R^2$ and n have the meanings given above, (b) cyclic boronic esters of the formula (A-b) in which m represents 2, p represents 1, Q represents a $C_1$-$C_4$-alkoxy group, where the two Q substituents together with the boron atom to which they are attached via the oxygen atom form a 5- or 6-membered ring which may be substituted by $C_1$-$C_4$-alkyl; preference is given to the groupings below:

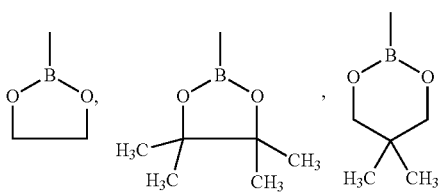

$R^2$ and n have the meanings given above,
(c) boronates of the formula (A-c) in which
m represents 3,
p represents 1,
Q represents hydroxy, fluorine, $C_1$-$C_4$-alkoxy or $C_6$-$C_{10}$-aryloxy and
where the negative charge of the boron anion is compensated by a cation;
$R^2$ and n have the meanings given above,
(d) a diphenylboric acid of the formula (A-d) in which
m represents 1,
p represents 2,
Q represents hydroxy, $C_1$-$C_4$-alkoxy or $C_6$-$C_{10}$-aryloxy and
$R^2$ and n have the meanings given above,
(e) a triaiylborate salt of the formula (A-e), in which
m represents 0,
p represents 3 and
$R^2$ and n have the meanings given above,
(f) a difluoroborate salt of the borinic acid of the formula (A-f), in which
m represents 2,
p represents 2,
Q represents fluorine,
where the negative charge of the boron anion is compensated by a cation,
$R^2$ and n have the meanings given above,
(g) a tetraarylborate salt of the formula (A-g), in which
m represents 0,
p represents 4,
where the negative charge of the boron anion is compensated by a cation;
$R^2$ and n have the meanings given above, The reaction of the boron compounds is preferably carried out in the presence of at least one solvent selected, for example, from the group consisting of water, aliphatic ethers, optionally halogenated aromatic or aliphatic hydrocarbons, alcohols, esters, aromatic or aliphatic nitriles and dipolar aprotic solvents such as dialkyl sulfoxides, N,N-dialkylamides of aliphatic carboxylic acids or alkylated lactams.

Particular preference is given to solvents selected from the group consisting of THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, anisol, ethyl acetate, isopropyl acetate, methanol, ethanol, propanol, butanol, ethylene glycol, ethylene carbonate, propylene carbonate, N,N-dimethylacetamide, N,N-dimethylformamide, N-methylpyrrolidone, water and mixtures of these.

Very particular preference is given to mixtures with the environmentally friendly solvent water.

Moreover, it has been observed that the addition of small amounts of water to the organic solvents contributes to a substantial suppression of the competing homocoupling reaction.

However, owing to the solubilities of the starting materials and the products formed, it is generally not possible to dispense entirely with the presence of a solvent. Accordingly, the organic solvents are preferably used as cosolvents.

The solvent mixtures according to the invention may comprise from 0.1 to 95% by volume and preferably from 1 to 60% by volume of water, based on the mixture of water and the organic solvent.

Since an acid is formed in the reaction, it is advantageous to scavenge the acid formed by addition of a base. The base may either be present from the beginning or metered in continuously during the reaction (semi-batch process), Suitable bases in accordance with the present invention are, for example, primary, secondary and tertiary amines such as, for example, alkylamines, dialkylamines, trialkylamines, which may be cyclic or open-chain; alkali metal and alkaline earth metal salts of aliphatic and/or aromatic carboxylic acids, such as acetates, propionates or benzoates; alkali metal and alkaline earth metal carbonates, bicarbonates, phosphates, hydrogenphosphates and/or hydroxides; and also metal alkoxides, in particular alkali metal or alkaline earth metal alkoxides, such as, for example, sodium methoxide, potassium methoxide, sodium ethoxide, magnesium methoxide, calcium ethoxide, sodium tert-butoxide, potassium tert-butoxide or alkali metal isoamylates. Preferably, the base is a carbonate, hydroxide or phosphate of lithium, sodium, potassium, calcium, magnesium or cesium. Particular preference is given to NaOH, KOH, potash and soda.

In addition to the neutralization of the acid formed, the base employed may also have a positive effect on the course of the reaction by activating the arylboronic acid to anionic boronate species. In addition to the bases mentioned above, such an activation may also be achieved by addition of fluoride salts such as, for example, CaF, NaF, KF, LiF, CsF or TBAF.

Suitable for use as catalytically active palladium catalysts or precatalysts are any palladium(II) compounds, palladium (0) compounds and palladium on any customary inorganic carrier material such as, for example, alumina, silica, zirconia, titanium dioxide or carbon, particularly preferably palladium on activated carbon. For the present process, it was found that an amount of from 0.0001 to 5 mol % of the catalytically active metal compound (calculated for the metal), preferably from 0.001 to 3 mol %, based on the starting material, is sufficient.

The palladium catalysts employed are generally generated in situ from at least one palladium(II) salt or a palladium(0) compound and the appropriate phosphine ligands. However, they may also be employed directly as palladium(0) compound without any reduction of the initial catalytic activity.

The heterogeneous palladium catalyst can be used as water-moist or dry powder or as water-moist or dry powder compressed to shaped articles.

Suitable palladium sources are, for example, selected from the group consisting of palladium trifluoroacetate, palladium fluoracetylacetonate, Pd(OAc)$_2$, Pd(OCOCH$_2$CH$_3$)$_2$, Pd(OH)$_2$, PdCl$_2$, PdBr$_2$, Pd(acac)$_2$ (acac=acetylacetonate), Pd(NO$_3$)$_2$, Pd(dba)$_2$, Pd$_2$dba$_3$ (dba=dibenzylideneacetone), Pd(CH$_3$CN)$_2$Cl$_2$, Pd(PhCN)$_2$Cl$_2$, Li[PdCl$_4$], Pd/C or palladium nanoparticles.

A preferred embodiment provides the use of methyl-di(C$_{3-8}$-alkyl)phosphine or tri(C$_{3-8}$-alkyl)phosphine ligands branched in the alkyl moiety or salts thereof, particularly preferably of methyl-di(tert-butyl)phosphine and tri(tert-butyl)phosphine as ligand.

The trialkylphosphine may also be employed as trialkylphosphonium salt such as, for example, as tetraluoroborate (Org. Lett. 2001, 3, 4295), perchlorate or hydrogensulfate and released therefrom in situ using a base.

The molar ratio of palladium to phosphine ligand should be between 4:1 and 1:100 and as preferably between 1:1 and 1:5, particularly preferably between 1:1 and 1:2.

However, according to the invention, it has also been possible to employ Pd[P(t-But)$_3$]$_2$, the preparation of which is described in (*JACS* 1976, 98, 5850; *JACS* 1977, 99, 2134; *JACS* 2001, 123, 2719), directly.

When carrying out the reaction, the catalyst system (Pd+ligand) can be added jointly or separately, either at room temperature or at elevated temperature. The system may be prepared separately shortly before the reaction by combining a Pd salt and the ligand (in situ process), or it may be added in crystalline form. It is also possible to add first the ligand and then the palladium salt directly to the reaction.

According to the present invention, the halogenated aromatics of the formula (II) and the boron compounds of the formulae (A-a) to (A-c) are employed in an equimolar ratio. However, alternatively, one of the two components (II or A), preferably the boron compounds (A-a) to (A-c), may be employed in excess. It is also possible to carry out the reaction in a meter-controlled manner, where one of the two reaction components is slowly metered in during the reaction. For this purpose, use is preferably made, for example, of a solution of the boronic acid or the boronate, while the halogen component, the catalyst and, if appropriate, the base are initially charged.

From the boron compounds of the formulae (A-d) and (A-f), from 0.5 to 0.7 equivalents (preferably 0.55 equivalents), based on the compound of the formula (II), are employed.

From the boron compounds of the formula (A-e), from 0.3 to 0.5 equivalents (preferably 0.35 equivalents), based on the compound of the formula (II), are employed.

From the boron compounds of the formula (A-g), from 0.25 to 0.4 equivalents (preferably 0.3 equivalents), based on the compound of the formula (II), are employed.

The reaction is generally carried out at a temperature between 10 and 200° C., preferably between 20 and 140° C., and at a pressure of up to 100 bar, preferably at a pressure between atmospheric pressure and 40 bar.

The reaction is preferably carried out with exclusion of atmospheric oxygen under an atmosphere of protective gas, for example under an argon or nitrogen atmosphere.

Owing to the catalyst activities and stabilities, it is possible to use extremely small amounts of catalyst in the process according to the invention, so that the catalyst costs, compared to the known Suzuki reactions, are not limited for the process in question.

In the process according to the invention, catalyst contents of from 0.0001 to 5 mol %, particularly preferably <0.1 mol %, based on the halogen component, are used.

Owing to the small amounts of catalyst, in most cases, the catalyst may remain in the end product. However, alternatively, there may also be a purification of the biaryls obtained by filtration, for example through celite.

Boronic acids of the formula (A-a) in which
m represents 2,
p represents 1,
Q represents a hydroxyl group and
$R^2$ and n have the meanings given above
can be obtained by reacting arylmagnesium halides (Grignard reagents) with trialkyl borates, preferably in a solvent such as, for example, THF. To suppress the competing formation of arylborinic acids, the reaction has to be carried out at low temperatures (−60° C.) and excess reagents have to be avoided, as described in R. M. Washburn et al., *Organic Syntheses Collective Vol.* 4, 68 or in Boronic Acids, Edited by Dennis G. Hall, Wiley-VCH 2005, p. 28ff.

Cyclic boronic esters of the formula (A-b), in which
m represents 2,
p represents 1,
Q represents in each case a $C_1$-$C_4$-alkoxy group, where the two Q atoms together with the boron atom to which they are attached via the oxygen atom form a 5- or 6-membered ring may be substituted by $C_1$-$C_4$-alkyl, can be prepared as described in Boronic Acids, Edited by Dennis G. Hall, Wiley-VCH 2005, p. 28ff.

Boronates of the formula (A-c) in which
m represents 3,
p represents 1,
Q represents hydroxyl, fluorine, $C_1$-$C_4$-alkoxy or $C_6$-$C_{10}$-aryloxy (preferably, Q represents fluorine) and
$R^2$ and n have the meanings given above,
where the negative charge of the boron anion is compensated by a cation, which is illustrated by the formula below:

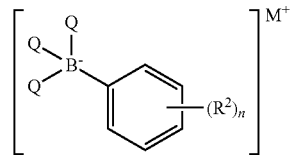

can be obtained as described in J. P. Genet et., *Chem. Rev.* 2008, 108, 288-325.

In the context of the present invention, the boronates of the general formula (A-c) contain a cation ($M^+$) selected from alkali metals and alkaline earth metals such as, for example, Li, Na, K, Cs, Mg, Ca and Ba or from tetraalkylammonium cations such as, for example, $NMe_4^+$, $NEt_4^+$, $NBu_4^+$ or from trialkylammonium cations such as $HNEt_3^+$ or $MgX^+$, preferably Na, K, Mg.

Diphenylborinic acids of the formula (A-d), in which
m represents 1,
p represents 2,
Q represents hydroxyl, $C_1$-$C_4$-alkoxy or $C_6$-$C_{10}$-aryloxy and
$R^2$ and n have the meanings given above,
can be obtained by reacting optionally substituted phenylmagnesium halide with trialkyl borate, as described in scheme 1.

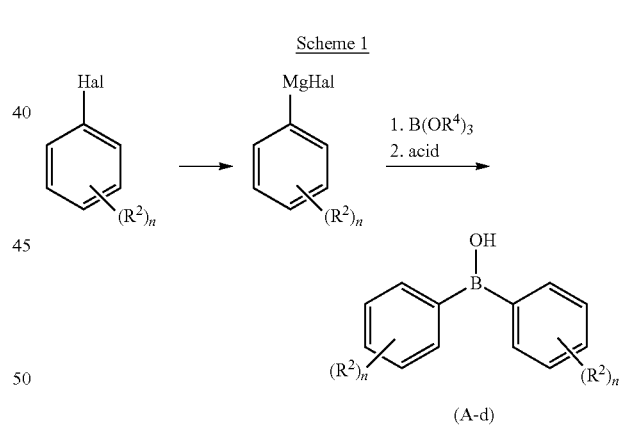

$R^2$ has the meanings given above,
Hal represents chlorine, bromine, iodine.

A particularly preferred starting material is bis(4-fluorophenyl)borinic acid.

This step of the process can be carried out at temperatures between 10 and 70° C.; preference is given to temperatures between 15 and 55° C.

Triarylborate salts of the formula (A-e), in which
m represents 0,
p represents 3 and
$R^2$ and n have the meanings given above
can be described as in H. C. Brown et al. J. Organomet Chem. 1988, 73, and in H. C. Brown et al. "Borane reagents", Harcourt Brace Jovanovich, Publishers, (1988).

Difluoroborate salts of borinic acid of the formula (A-f), in which
m represents 2,
p represents 2,
Q represents fluorine,
where the negative charge of the boron anion is compensated by a cation selected from alkali metals and alkaline earth metals such as, for example, Li, Na, K, Cs, Mg, Ca and Ba or from tetraalkylammonium cations such as, for example, $NMe_4^+$, $NEt_4^+$, $NBu_4^+$ or from trialkylammonium cations such as $HNEt_3^+$ or $MgX^+$, preferably Na, K, Mg,
$R^2$ and n have the meanings given above,
can be obtained as described in T. Ito et al., *Synlett* 2003, No. 10, 1435-1438.

Tetraarylborate salts of the formula (A-g), in which
m represents 0,
p represents 4,
$R^2$ and n have the meanings given above,
where the negative charge of the boron anion is compensated by a cation selected from alkali metals and alkaline earth metals such as, for example, Li, Na, K, Cs, Mg, Ca and Ba or from tetraalkylammonium cations such as, for example, $NMe_4^+$, $NEt_4^+$, $NBu_4^+$ or from trialkylammonium cations such as $HNEt_3^+$ or $MgX^+$, preferably Na, K, Mg,
can be obtained as described in J. Serwatowski et al., *Tetrahedron Lett.* 2003, 44, 7329.

The general or preferred radical definitions or illustrations given above can be combined with one another as desired, i.e. including combinations between the respective ranges and preferred ranges.

The compounds of the formulae (I), (II), (III) and (IV) are known from the prior art, for example WO 97/36868, WO 2005/016873, WO 2008/067911, Recueil des Travaux Chimiques des Pays-Bas et de la Belgique, 79, 1960, 1211-1222, Acta Chemica Scandinavica, 17, 5, 1963, 1252-1261, Bulletin de la Societe Chimique de France, 9, 1942, 889-892).

The preparation of the biphenyl compounds by the process according to the invention is to be illustrated by the preparation examples.

PREPARATION EXAMPLES

Example 1

4-tert-Butyl-2,6-dimethylmandelic acid acetate

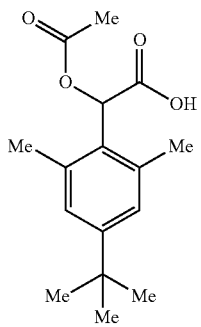 [SMILES: CC(=O)OC(C(=O)O)c1c(C)cc(C(C)(C)C)cc1C]

A mixture of 89 g of 50% aqueous glyoxylic acid solution [0.6 mol], 400 ml of glacial acetic acid and 81.1 g [0.5 mol] of 1-tert-butyl-3,5-dimethylbenzene is initially charged. Starting at room temperature, 85.8 g of 96% strength sulfuric acid [0.84 mol] are added dropwise over a period of 15 minutes, during which time the temperature of the reaction mixture increases to about 35° C. The mixture is heated to 60° C. and stirred at this temperature for 9 hours. The cooled reaction mixture is then stirred into 750 ml of ice-water. The mixture is extracted three times with in each case 150 ml of methylene chloride, the combined organic phases are washed with 100 ml of saturated aqueous NaCl solution, dried over sodium sulfate and concentrated under reduced pressure. This gives 136.7 g of a yellowish thick oil, which, according to GC/MS (sil.), has the following composition:
  2.6 area % of 1-tert-butyl-3,5-dimethylbenzene (4.4% of the starting material employed)
  23.7 area % of 4-tert-butyl-2,6-dimethylmandelic acid (27.4% of theory)
  67.2 area % of 4-tert-butyl-2,6-dimetlylmandelic acid acetate (66% of theory)

Comparative Example 1

1-(4-tert-Butyl-2,6-dimethylphenyl)-2,2-dichloroethanone

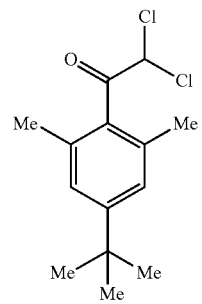 [SMILES: Cc1cc(C(C)(C)C)cc(C)c1C(=O)C(Cl)Cl]

4.06 g [25 mmol] of 5-tert-butyl-2,6-dimethylbenzene and 4 g [27 mmol] of dichloroacetyl chloride are initially charged in 25 ml of carbon disulfide. With exclusion of atmospheric moisture, 10 g [75 mmol] of $AlCl_3$ are then added a little at a time at 10-15° C. over a period of about 25 minutes. The mixture is then stirred at 10-15° C. for 2 hours, allowed to warm to room temperature and stirred for a further 2 hours. The reaction mixture is diluted with about 50 ml of methylene chloride and stirred into ice-water. The phases are separated, the aqueous phase is extracted with 30 ml of methylene chloride, the combined organic phases are washed with 25 ml of saturated aqueous NaCl solution, dried over sodium sulfate and concentrated under reduced pressure. This gives 6.4 g of a brown oil which, according to GC/MS, comprises 7.9 area % of 1-(4-tert-butyl-2,6-dimethylphenyl)-2,2-dichloroethanone (7.4% of theory).

Example 2

4-tert-Butyl-2,6-dimethylmandelic acid

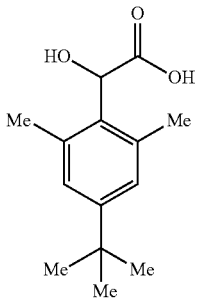 [SMILES: Cc1cc(C(C)(C)C)cc(C)c1C(O)C(=O)O]

127.4 g of a mixture comprising 64.2 area % of 4-tert-butyl-2,6-dimethylmandelic acid acetate and 24.8 area % of 4-tert-butyl-2,6-dimethylmandelic acid are initially charged in 335 ml of water. The mixture is heated to 65° C., and at 75-80° C., 163.7 g of 45% strength aqueous sodium hydroxide solution are then added dropwise. After 4 hours at 80° C., the mixture is allowed to cool to room temperature, 196 g of 48% strength sulfuric acid are added dropwise, the suspension is stirred with 500 ml of water, the solid is filtered off with suction and washed four times with in each case 100 ml of water. After drying, about 100 g of a solid remain.

$^1$H-NMR (d$_6$-DMSO): δ=1.24 (s, 9H), 2.30 (s, 6H), 5.35 (s, 1H), 6.98 (s, 2H) ppm.

m.p.:120.5-122° C.

Example 3

4-tert-Butyl-2,6-dimethylphenylacetic acid

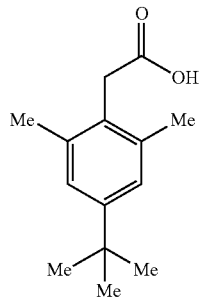 [SMILES: Cc1cc(C(C)(C)C)cc(C)c1CC(=O)O]

A mixture of 47.2 g of 4-tert-butyl-2,6-dimethylmandelic acid [0.2 mol], 7 g of 37% strength hydrochloric acid, 9.3 g of red phosphorus and 33 g of KI in 150 ml of glacial acetic acid is heated at 100° C. for 16 hours. The excess of phosphorus is filtered off with suction and washed three times with in each case 70 ml of glacial acetic acid. The filtrate is substantially concentrated on a rotary evaporator at a bath temperature of 50° C./60 mbar. The resulting residue is stirred in 180 ml of water and, by addition of about 215 g of 10% strength aqueous sodium hydroxide solution, dissolved. This solution is extracted twice with in each case 150 ml of methyl tert-butyl ether (MTBE) and then adjusted to pH 1 using 48% strength sulfuric acid. The precipitated solid is filtered off with suction, washed four times with in each case 50 ml of water and dried. This gives 37.2 g of 4-tert-butyl-2,6-dimethylphenylacetic acid in a purity of 99.1 GC area % (yield about 83.6% of theory).

$^1$H-NMR (d$_6$-DMSO): δ=1.29 (s, 9H), 2.33 (s, 6H), 3.68 (s, 2H), 7.05 (s, 2H) ppm.

m.p.:163.5-164.5° C.

Example 4

4-tert-Butyl-2,6-dimethylphenylacetic acid

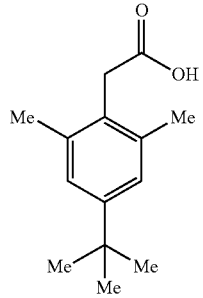 [SMILES: Cc1cc(C(C)(C)C)cc(C)c1CC(=O)O]

A mixture of 2.89 g of 4-tert-butyl-2,6-dimethylmandelic acid and 7.75 g of 4-tert-butyl-2,6-dimethylmandelic acid acetate, 4.5 g of 37% strength hydrochloric acid, 1.86 g of red phosphorus and 0.66 g of KI in 30 ml of glacial acetic acid is heated at 100° C. for 16 hours. Excess phosphorus is filtered off with suction and washed three times with in each case 10 ml of glacial acetic acid. The filtrate is substantially concentrated on a rotary evaporator at a bath temperature of 50° C./60 mbar. The resulting residue is diluted with 25 ml of water and, by addition of 10% strength aqueous sodium hydroxide solution, dissolved. This solution is extracted twice with in each case 20 ml of MTBE and then adjusted to pH 1 using 48% strength sulfuric acid. The resulting greasy solid is taken up in methylene chloride. This solution is extracted with 25 ml of water, dried over sodium sulfate and concentrated using a rotary evaporator. This gives 7.66 g of 4-tert-butyl-2,6-dimethylphenylacetic acid in a purity of 99.0 GC area % (yield about 86% of theory).

Example 5

2,6-Dimethylphenylacetic acid

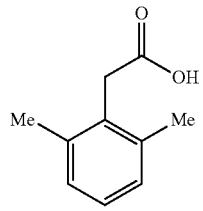 [SMILES: Cc1cccc(C)c1CC(=O)O]

16.52 g [75 mmol] of 4-tert-butyl-2,6-dimethylphenylacetic acid and 100 ml of toluene are initially charged in a 250 ml autoclave. After cooling to 0° C., 40 ml of HF are added and the autoclave is closed. The reaction mixture is then stirred at 38-40° C. for 4 hours. Toluene and HF are then distilled off at 20° C./100 mbar. The residue is diluted with 65 ml of water and, with ice-cooling, made alkaline using 100 ml of 10% strength aqueous sodium hydroxide solution. The solution is extracted once with 65 ml of MTBE and once with 35 ml of MTBE, the aqueous phase is then, with ice-cooling, adjusted to pH 1 using 32% strength hydrochloric acid, then precipitate formed is dissolved in 130 ml of methylene chloride, the organic phase is dried and the solvent is removed under reduced pressure. This gives 11.91 g of a white solid which, according to GC(sil.), comprises 95.8% of 2,6-dimethylphenylacetic acid (92.6% of theory).

Example 6

3-Bromo-2,6-dimethylphenylacetic acid

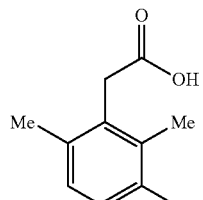

At 45° C., a solution of 62.5 g [391 mmol] of bromine in 120 ml of glacial acetic acid is added dropwise over a period of 1 hour to a solution of 47.6 g [290 mmol] of 2,6-dimethylphenylacetic acid in 300 ml of glacial acetic acid. The reaction mixture is then stirred at 45° C. for another 16 hours and concentrated on a rotary evaporator. The solid obtained is stirred in 180 ml of methylcyclohexane at room temperature for 4 hours. After filtration, the residue is washed twice with in each case 60 ml of methylcyclohexane and then dried. This gives 64.9 g of a solid. GC(sil.) analysis: 97.7% pure (89.9% of theory).

Example 7

3-Bromo-2,6-dimethylphenylacetic acid

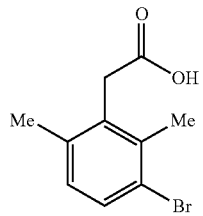

At 45° C., a solution of 8.5 kg [53.2 mol] of bromine in 10 l of glacial acetic acid is added dropwise to a solution of 6.86 kg [40.45 mol] of 2,6-dimethylphenylacetic acid in 40 l of glacial acetic acid. The reaction mixture is then stirred at 45° C. for another 16 hours and concentrated on a rotary evaporator. The solid obtained is stirred in 10 l of cyclohexane at room temperature. After filtration, the residue is washed a little at a time with 10 l of cyclohexane and then dried. This gives 8.43 kg of a solid.

GC analysis: 99.3% pure (85.3% of theory).

Example 8

Methyl 3-bromo-2,6-dimethylphenylacetate

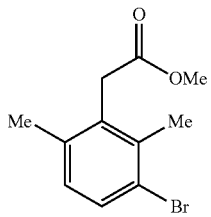

At about 15° C., a solution of 3.67 kg [23 mol] of bromine in 9 l of glacial acetic acid is added dropwise to a solution of 3.175 kg [17.82 mol] of methyl 2,6-dimethylphenylacetate in 18 l of glacial acetic acid. The mixture is then stirred at 15° C. for another 2.5 hours, in order to warm to room temperature and stirred at room temperature for 48 hours. The reaction mixture is poured into 170 l of ice-water and extracted twice with in each case 60 l of methylene chloride. After removal of the solvent, 4 kg of a residue remain which, according to GC/MS, comprise 81.2% of methyl 3-bromo-2,6-dimethylphenylacetate (70.9% of theory),

Comparative Example 2

3-Chloro-2,6-dimethylphenylacetic acid

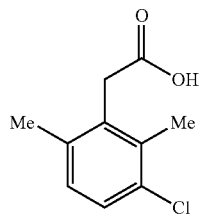 [SMILES: Cc1ccc(Cl)c(C)c1CC(=O)O]

At 10-15° C., 9.22 g [130 mmol] of chlorine gas are slowly introduced into a solution of 16.4 g [100 mmol] of 2,6-dimethylphenylacetic acid in 100 ml of glacial acetic acid. The reaction mixture is then stirred at room temperature for 16 hours and then poured into 500 ml of water. The precipitated solid is filtered off with suction, washed with water and dried. This gives 18.8 g of a white solid which, according to GC(sil.), has the following composition: 86.4% of 3-chloro-2,6-dimethylphenylacetic acid (corresponds to a yield of 81.8% of theory), 8.8% of dichloro-2,6-dimethylphenylacetic acid (isomer 1), 3.8% of dichloro-2,6-dimethylphenylacetic acid (isomer 2).

Preparation of (4'-fluoro-2,4-dimethylbiphenyl-3-yl)acetic acid from 4-fluorophenylboronic acid

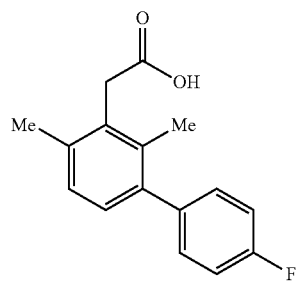 [SMILES: Cc1ccc(-c2ccc(F)cc2)c(C)c1CC(=O)O]

With exclusion of oxygen, 101.6 g [415 mmol] of (3-bromo-2,6-dimethylphenyl)acetic acid, 59.26 g [415 mmol] of 4-fluorophenylboronic acid and 2.67 g [8.29 mmol] of n-tetrabutylammonium bromide are suspended in a mixture of 74.1 g [833 mmol, 45% strength] of sodium hydroxide solution and 210 g of water under argon. 218 mg [0.205 mmol] of palladium on carbon [10%] are added, and the reaction mixture is stirred at 90° C. for 12 hours. After the reaction has ended (monitored by GC), the reaction mixture is cooled to about 40° C. and 22.8 g of sodium hydroxide solution [45% strength] and 50 g of cyclohexane are added. The organic phase is separated off at 40° C. and concentrated under reduced pressure. This gives 312 mg of 4,4'-difluorobiphenyl.

The aqueous phase is admixed with 200 g of toluene and then adjusted to pH 1.25 using 32% strength hydrochloric acid. The suspension is heated to 65° C., and the organic phase is separated off at this temperature. The aqueous phase is extracted at 65° C. with 200 g of toluene, and the combined organic phases are then filtered through Celite, the Celite is washed with 100 g of toluene and the filtrate is cooled to about 5° C. The precipitated solid is filtered off with suction and washed with pre-cooled toluene and dried. This gives 101.2 g [98.6% pure, 93% of theory] of 4'-fluoro-2,4-dimethylbiphenyl-3-yl)acetic acid.

$^1$H-NMR (d$_6$-DMSO): δ=2.11 (s, 3H), 2.29 (s, 3H), 3.68 (s, 2H), 6.97-7.30 (m, 6H), 12.36 (s, 1H) ppm.

Preparation of (4'-fluoro-2,4-dimethylbiphenyl-3-yl)acetic acid from 4-fluorophenyltrifluoroborate potassium salt With exclusion of oxygen, 4.50 g [18.34 mmol] of (3-bromo-2,6-dimethylphenyl)acetic acid, 3.94 g [19.48 mmol] of 4-fluorophenyltrifluoroborate potassium salt and 59.2 mg [0.18 mmol] of n-tetrabutylammonium bromide are suspended in a mixture of 3.43 g [38.61 mmol, 45% strength] of sodium hydroxide solution, 4 g of n-butanol and 20 g of water under argon. 9.78 mg of palladium on carbon [10%] are added, and the reaction mixture is stirred at 84° C. for 12 hours. After the reaction has ended (monitored by GC), the reaction mixture is cooled to room temperature and 5 g of water and 40 g of ethyl acetate are added. Using 32% strength hydrochloric acid, the pH of the mixture is adjusted to 2, and the mixture is then filtered through Celite. The organic phase is separated off and the aqueous phase is extracted with ethyl acetate. The combined organic phases are dried and concentrated. This gives 3.8 g of a white solid which, according to GC-MS, has the following composition: 94.1% of (4'-fluoro-2,4-dimethylbiphenyl-3-yl)acetic acid and 3.4% of (3-bromo-2,6-dimethylphenyl)acetic acid.

Preparation of (4'-fluoro-2,4-dimethylbiphenyl-3-yl) acetic acid from bis(4-fluorophenyl)borinic acid With exclusion of oxygen, 6 g [24.5 mmol] of (3-bromo-2,6-dimethylphenyl)acetic acid, 3 g [13.5 mmol] of bis(4-fluorophenyl)borinic acid and 79 mg [0.24 mmol] of n-tetrabutylammonium bromide are suspended in a mixture of 4.58 g [51 mmol, 45% strength] of sodium hydroxide solution, 3.24 g of n-butanol and 20 g of water under argon. 13 mg [0.012 mmol] of palladium on carbon [10%] are added, and the reaction mixture is stirred at 85° C. for 12 hours. After the reaction has ended (monitored by GC), the reaction mixture is cooled to RT and 10 g of water and 50 g of ethyl acetate are added. The pH of the mixture is adjusted to 1.5 using 32% strength hydrochloric acid. The organic phase is separated off and the aqueous phase is extracted with ethyl acetate. The combined organic phases are dried and concentrated. This gives 6.81 g of (4'-fluoro-2,4-dimethylbiphenyl-3-yl)acetic acid [89.8% pure, 96.4% of theory].

Preparation of (4'-fluoro-2,4-dimethylbiphenyl-3-yl) acetic acid from difluoro[bis(4-fluorophenyl)]borate potassium salt With exclusion of oxygen, 2.9 g [11.85 mmol] of (3-bromo-2,6-dimethylphenyl)acetic acid, 1.98 g [7.1 mmol] of difluoro[bis(4-fluorophenyl)]borate potassium salt and 38.2 mg [0.12 mmol] of n-tetrabutylammonium bromide are suspended in a mixture of 2.21 g [24.88 mmol, 45% strength] of sodium hydroxide solution, 2.3 g of n-butanol and 12 g of water. 6.3 mg [0.006 mmol] of palladium on carbon [10%] are added, and the reaction mixture is stirred at 85° C. for 12 hours. After the reaction has ended (monitored by GC), the reaction mixture is cooled to RT and 7 g of water and 40 g of ethyl acetate are added. The pH of the mixture is adjusted to 1.5 using 32% strength hydrochloric acid. The organic phase is separated off and the aqueous phase is extracted with ethyl acetate. The combined organic phases are dried and concentrated. This gives 3 g of (4'-fluoro-2,4-dimethylbiphenyl-3-yl)acetic acid [98% of theory].

Preparation of (4'-fluoro-2,4-dimethylbiphenyl-3-yl) acetic acid from sodium tetrakis(4-fluorophenyl) borate dihydrate With exclusion of oxygen, 350 mg [1.44 mmol] of (3-bromo-2,6-dimethylphenyl)acetic acid, 198 mg [0.43 mmol] of sodium tetrakis(4-fluorophenyl)borate dihydrate and 4.6 mg [0.014 mmol] of n-tetrabutylammonium bromide are suspended in a mixture of 268 mg [3.02 mmol, 45% strength] of sodium hydroxide solution, 405 mg of n-butanol and 2 g of water under argon. 1.53 mg of palladium on carbon [10%] are added, and the reaction mixture is stirred at 90° C. for 12 hours. After the reaction has ended (monitored by GC), the reaction mixture is cooled to RT and 1 g of water and 20 g of ethyl acetate are added. The pH of the mixture is adjusted to 1.5 using 32% strength hydrochloric acid and the mixture is then filtered through Celite. The organic phase is separated off and the aqueous phase is extracted with ethyl acetate. The combined organic phases are dried and concentrated. This gives a white solid which, according to GC-MS, has the following composition; 1.6% of 4,4'-difluorobiphenyl, 0.78% of (2,6-dimethylphenyl)acetic acid and 96.44% of (4'-fluoro-2,4-dimethylbiphenyl-3-yl)acetic acid [98% of theory].

The invention claimed is:

1. A process for preparing a compound of formula (I), characterized in that 1-tert-butyl-3,5-dimethylbenzene is reacted with a compound of formula (VI) to give a compound of the formula (V) which is subsequently reduced to a compound of formula (IV); the compound of formula (IV) is converted by removal of the tert-butyl radical into a compound of formula (III), and bromination of the compound of formula (III) gives a compound of formula (II) which, using a compound of formula (A) in the presence of a base and a palladium catalyst, optionally in a solvent, is converted into a biphenyl compound of formula (I):

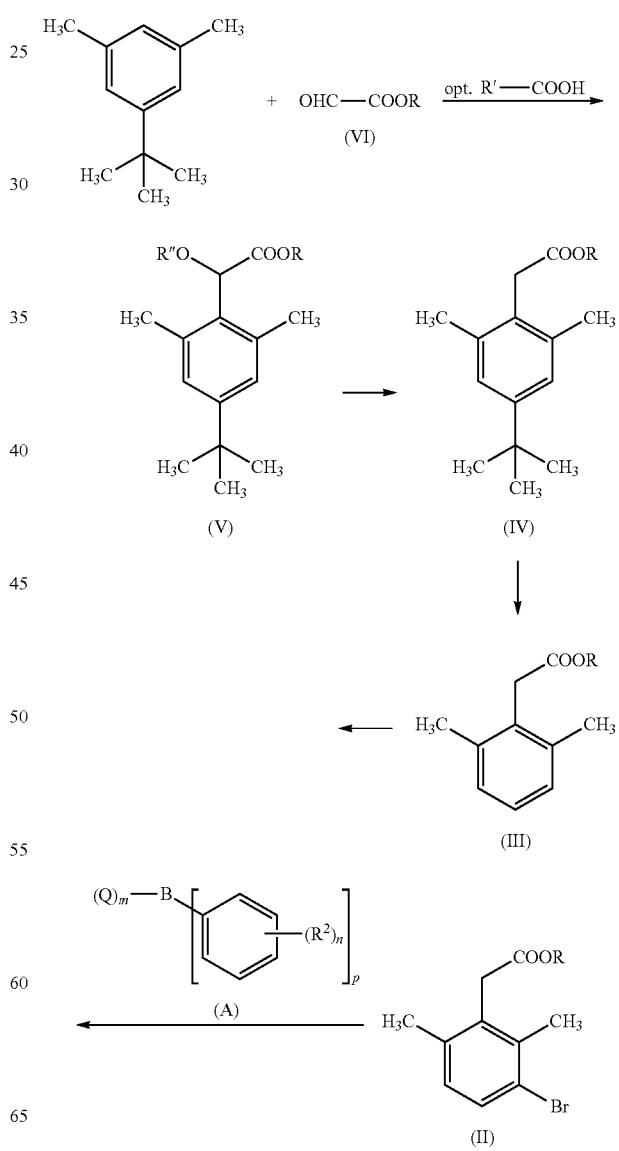

-continued

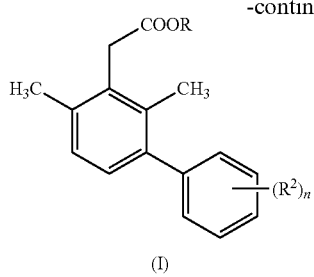

(I)

in which
R represents hydrogen, $C_1$-$C_6$-alkyl or phenyl,
R' represents hydrogen or $C_1$-$C_6$-alkyl,
R" represents hydrogen or a radical R'CO,
$R^2$ represents hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, cyano, or nitro,
n represents 0, 1, 2 or 3,
and
A is selected from the groups below:

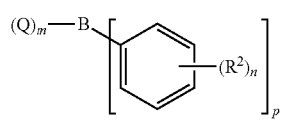

(a) boronic acid of the formula (A-a), in which
m represents 2,
p represents 1,
Q represents a hydroxyl group, or the anhydrides, dimers and trimers formed therefrom, and
$R^2$ and n are as defined above,
(b) cyclic boronic esters of the formula (A-b), in which
m represents 2,
represents 1,
Q represents a $C_1$-$C_4$-alkoxy group, where the two Q substituents together with the boron atom to which they are attached via the oxygen atom form a 5- or 6-membered ring which is optionally substituted by $C_1$-$C_4$-alkyl, and
$R^2$ and n are as defined above,
(c) boronates of the formula (A-c), in which
m represents 3,
p represents 1,
Q represents hydroxy, fluorine, $C_1$-$C_4$-alkoxy or $C_6$-$C_{10}$-aryloxy and
where the negative charge of the boron ion is compensated by a cation, and
$R^2$ and n are as defined above,
(d) a diphenylboric acid of the formula (A-d), in which
m represents 1,
p represents 2,
Q represents hydroxy, $C_1$-$C_4$-alkoxy or $C_6$-$C_{10}$-aryloxy, and
$R^2$ and n are as defined above,
(e) a triarylborate salt of the formula (A-e), in which
m represents 0,
p represents 3, and
$R^2$ and n are as defined above,
(f) a difluoroborate salt of the borinic acid of the formula (A-f), in which
m represents 2,
p represents 2,
Q represents fluorine, where the negative charge of the boron ion is compensated by a cation, and
$R^2$ and n are as defined above,
(g) a tetraarylborate salt of the formula (A-g), in which
m represents 0,
p represents 4,
where the negative charge of the boron anion is compensated by a cation, and
$R^2$ and n are as defined above.

2. The process as claimed in claim 1, where
R represents hydrogen or $C_1$-$C_6$-alkyl,
R' represents $C_1$-$C_6$-alkyl,
R" represents hydrogen or a radical R'CO,
$R^2$ represents hydrogen, halogen or $C_1$-$C_4$-alkyl, and
n represents 0, 1, 2 or 3.

3. The process as claimed in claim 1, where
R represents hydrogen or methyl,
R' represents $C_1$-$C_6$-alkyl,
R" represents hydrogen or a radical R'CO,
$R^2$ represents hydrogen or fluorine, and
n represents 0, 1, 2 or 3.

4. The process as claimed in claim 1, where
R represents hydrogen,
R' represents methyl,
R" represents hydrogen or a radical R'CO,
$R^2$ represents fluorine, and
n represents 1.

5. A process for preparing a compound of formula (IV)

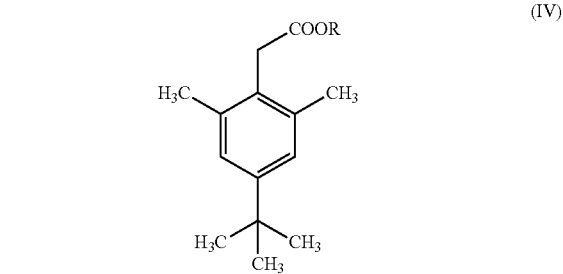

in which
R represents hydrogen, $C_1$-$C_6$-alkyl or phenyl,
characterized in that 4-tert-butyl-3,5-dimethylbenzene is reacted with a compound of formula (VI)

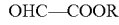

in which R is as defined above,
in the presence of R'—COOH, where
R' represents hydrogen or $C_1$-$C_6$-alkyl,
to give a compound of formula (V)

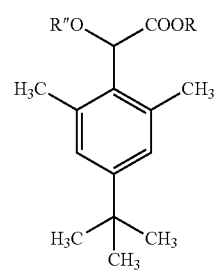

in which
R" represents hydrogen or a radical R'CO, and R is, as defined above,
and the compound of formula (V) is then reduced.

6. A compound of formula (V)

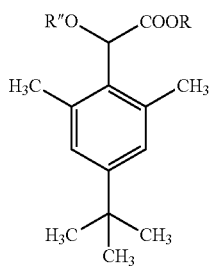

in which
R represents hydrogen, $C_1$-$C_6$-alkyl or phenyl,
R" represents hydrogen or a radical R'CO, and
R' represents hydrogen or $C_1$-$C_6$-alkyl.

7. A process for preparing a compound of formula (III)

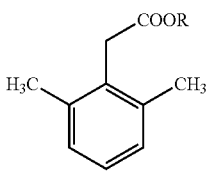

in which
R represents hydrogen, $C_1$-$C_6$-alkyl or phenyl,
comprising, removing the tert-butyl radical from a compound of formula (IV)

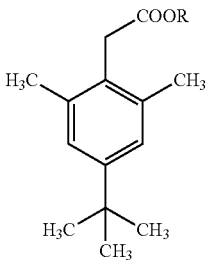

in which R is as defined above.

8. A process for preparing a compound of formula (II)

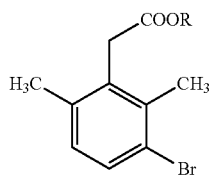

in which
R represents hydrogen, $C_1$-$C_6$-alkyl or phenyl,
comprising, brominating a compound of formula (III)

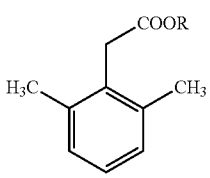

in which R is as defined above.

9. A process for preparing a compound of formula (I)

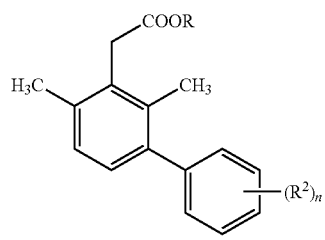

in which
R represents hydrogen, $C_1$-$C_6$-alkyl or phenyl,
$R^2$ represents hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, cyano, or nitro
and
n represents 0, 1, 2 or 3,
comprising, reacting a compound of formula (II)

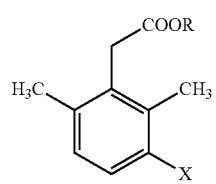

in which
R is as defined above, and
X represents halogen,
in the presence of a base and a palladium catalyst, optionally in a solvent, with a compound of formula (A)

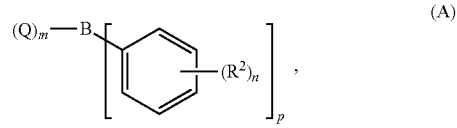

where A is selected from the groups below:
(a) boronic acid of the formula (A-a), in which
m represents 2,
p represents 1,
Q represents a hydroxyl group, or the anhydrides, dimers and trimers formed therefrom, and
$R^2$ and n are as defined above,
(b) cyclic boronic esters of the formula (A-b), in which
m represents 2,
p represents 1,
Q represents a $C_1$-$C_4$-alkoxy group, where the two Q substituents together with the boron atom to which they are attached via the oxygen atom form a 5- or 6-membered ring which may be substituted by $C_1$-$C_4$-alkyl, and
$R^2$ and n are as defined above,
(c) boronates of the formula (A-c), in which
m represents 3,
p represents 1,
Q represents hydroxy, fluorine, $C_1$-$C_4$-alkoxy or $C_6$-$C_{10}$-aryloxy and
where the negative charge of the boron anion is compensated by a cation, and
$R^2$ and n are as defined above,
(d) a diphenylboric acid of the formula (A-d), in which
m represents 1,
p represents 2, Q represents hydroxy, $C_1$-$C_4$-alkoxy or $C_6$-$C_{10}$-aryloxy, and $R^2$ and n are as defined above, (e) a triarylborate salt of the formula (A-e), in which m represents 0, p represents 3, and $R^2$ and n are as defined above, (f) a difluoroborate salt of the bonnie acid of the formula (A-f), in which m represents 2, p represents 2, Q represents fluorine, where the negative charge of the boron anion is compensated by a cation, and $R^2$ and n have are as defined above, (g) a tetraarylborate salt of the formula (A-g), in which m represents 0, p represents 4, where the negative charge of the boron anion is compensated by a cation, and $R^2$ and n are as defined above.

\* \* \* \* \*